(12) United States Patent
Brandeis (10) Patent No.: US 10,159,472 B2
(45) Date of Patent: Dec. 25, 2018

(54) METHOD AND DEVICE FOR VEIN ABLATION

(75) Inventor: Zeev Brandeis, Rosh HaAyin (IL)

(73) Assignee: V.V.T. Med Ltd., Kfar-Saba (IL)

(*) Notice: Subject to any disclaimer, the term of this patent is extended or adjusted under 35 U.S.C. 154(b) by 796 days.

(21) Appl. No.: 12/920,335

(22) PCT Filed: Mar. 2, 2009

(86) PCT No.: PCT/IL2009/000241
§ 371 (c)(1),
(2), (4) Date: Aug. 31, 2010

(87) PCT Pub. No.: WO2009/109967
PCT Pub. Date: Sep. 11, 2009

(65) Prior Publication Data
US 2011/0046543 A1 Feb. 24, 2011

Related U.S. Application Data

(60) Provisional application No. 61/032,978, filed on Mar. 2, 2008.

(51) Int. Cl.
*A61B 17/00* (2006.01)
*A61B 17/3207* (2006.01)
*A61B 17/32* (2006.01)

(52) U.S. Cl.
CPC .... *A61B 17/00008* (2013.01); *A61B 17/3207* (2013.01); *A61B 2017/00778* (2013.01); *A61B 2017/320012* (2013.01); *A61B 2017/320741* (2013.01)

(58) Field of Classification Search
CPC .. A61B 17/00008; A61B 2017/320741; A61B 2017/320012; A61B 17/3207; A61B 2017/00778

USPC .......... 604/22, 27–28, 36, 46–47, 509, 510, 604/95.01–95.05, 96.01, 181, 183–184
See application file for complete search history.

(56) References Cited

U.S. PATENT DOCUMENTS

| | | | |
|---|---|---|---|
| 5,370,653 A | | 12/1994 | Cragg |
| 5,941,871 A | * | 8/1999 | Adams et al. ............... 604/523 |
| 6,022,336 A | * | 2/2000 | Zadno-Azizi et al. .. 604/101.05 |
| 6,168,579 B1 | | 1/2001 | Tsugita |
| 6,652,548 B2 | * | 11/2003 | Evans et al. .................. 606/159 |

(Continued)

FOREIGN PATENT DOCUMENTS

| WO | WO 2004/112569 | 12/2004 |
|---|---|---|
| WO | WO 2006/134354 | 12/2006 |
| WO | WO 2009/109967 | 9/2009 |

OTHER PUBLICATIONS

International Preliminary Report on Patentability dated Sep. 16, 2010 From the International Bureau of WIPO Re. Application No. PCT/IL2009/000241.

(Continued)

*Primary Examiner* — Lauren P Farrar (57) ABSTRACT

A method for collapsing a target vein in a patient. The method comprises providing an intravascular irritation element having a plurality of mechanical irritating objects, inserting the intravascular irritation element into a venous lumen of a target vein, and irritating the target vein by moving the plurality of mechanical irritating objects in contact with the inner surface thereof, thereby triggering a collapse of the target vein.

27 Claims, 6 Drawing Sheets

(56) References Cited

U.S. PATENT DOCUMENTS

| | | | |
|---|---|---|---|
| 6,755,813 B2* | 6/2004 | Ouriel et al. | 604/537 |
| 6,878,142 B2* | 4/2005 | Lawrence et al. | 604/540 |
| 2007/0198028 A1* | 8/2007 | Miloslayski et al. | 606/127 |

OTHER PUBLICATIONS

International Search Report dated Jun. 5, 2009 From the International Searching Authority Re.: Application No. PCT/IL2009/000241.
Written Opinion dated Jun. 5, 2009 From the International Searching Authority Re.: Application No. PCT/IL2009/000241.
Communication Pursuant to Article 94(3) EPC dated Jan. 16, 2013 From the European Patent Office Re. Application No. 09718042.6.
Translation of Notice of Reason for Rejection dated Sep. 20, 2013 From the Japanese Patent Office Re. Application No. 2010-549258.
Translation of Reason for Rejection dated May 24, 2013 From the Japanese Patent Office Re. Application No. 2010549258.

* cited by examiner

METHOD AND DEVICE FOR VEIN ABLATION

RELATED APPLICATION/S

This Application is a National Phase of PCT Patent Application No. PCT/IL2009/000241 having International filing date of Mar. 2, 2009, which claims the benefit of U.S. Provisional Patent Application No. 61/032,978 filed on Mar. 2, 2008. The contents of the above Applications are all incorporated herein by reference.

FIELD AND BACKGROUND OF THE INVENTION

The present invention, in some embodiments thereof, relates to method and device for vein treatment and, more particularly, but not exclusively, to a method and a device for vein ablation.

Varicose veins occur when weak veins near the surface of the leg stretch, bulge, and twist. Varicose veins can be visible through the skin. In varicose veins, the valves arc malfunctioning or destroyed so that the veins balloon at the lower ends. This condition can be particularly pronounced in certain leg veins. Various methods have been developed for performing varicose vein ablation.

For example, one commonly used treatment is known as stripping surgical procedure. In a conventional stripping for the treatment of varicose veins, two incisions are made in a vein, one at the ankle and one at the groin. An elongate stripper instrument is then inserted through the ankle incision and passed through the vein to the groin. At the groin, a cup is attached to the distal end of the stripper. Subsequently, the stripper is pulled down the leg so that the cup rips out the vein. In this procedure, other veins connecting to the varicose vein are torn.

Another commonly used treatment is based on laser, electric or radio-frequency energy. When laser is used, bursts of radiofrequency or laser energy are sent through a catheter; the resulting heat intentionally destroys vein wall tissues along the length of the vein.

Other methods have been developed during the years. For example, U.S. Pat. No. 6,402,745 issued on Jun. 11, 2002 describes an intravenous surgical instrument comprises an inner shaft or post and an outer sheath. A spring-tail or whip-like electrode is disposed at a distal end of the inner post, substantially in a sagittal plane, or one perpendicular to a longitudinal axis of the shaft. Following an insertion into a human vein or other circulatory vessel the distal end of the shaft is protruded from the sheath; thereafter sheath, post and electrode are simultaneously withdrawn from the vein, with a relative rotatory motion being imparted to the electrode. A current flow is preferably simultaneously imposed across the electrode into an inner surface of the surrounding vessel, facilitating a damaging of the vessel inner surface and a collapse of the vessel. This description applies primarily to veins, which may be drained of blood prior to a start of a collapsing procedure; for use in arteries a modified embodiment is disclosed employing a compound construction electrode tip which facilitates a limiting of current flow to a region of direct electrode contact with a circulatory vessel wall, and a reduction of stray currents conduction into the blood.

Another example is described in U.S. Pat. No. 7,326,206, issued on Feb. 5, 2008, that describes brush electrode catheter and a method for using the brush electrode catheter for tissue ablation. The brush electrode catheter comprises a plurality of flexible filaments or bristles for applying ablative energy (e.g., RF energy) to target tissue during the formation of spot or continuous linear lesions. Interstitial spaces are defined among the filaments of the brush electrode, and the interstitial spaces are adapted to direct conductive or nonconductive fluid, when present, toward the distal ends of the brush filaments. The brush electrode facilitates electrode-tissue contact in target tissue having flat or contoured surfaces. The flexible filaments may be selectively trimmed to give a desired tip configuration or a desired standoff distance between the tissue and the conductive filaments in the brush electrode. Also, the filaments may be grouped into clusters. A shielded-tip brush electrode, including a flexible boot, is also disclosed.

SUMMARY OF THE INVENTION

According to some embodiments of the present invention there is provided a method for collapsing a target vein in a patient. The method comprises providing an intravascular irritation element having a plurality of mechanical irritating objects, inserting the intravascular irritation element into a venous lumen of a target vein, and irritating the target vein by moving the intravascular irritation element in contact with an inner surface thereof so that a collapse of the target vein is triggered.

Optionally, the target vein is the saphenous vein.

Optionally, the inserting comprises inserting the intravascular irritation element in a narrowed configuration and the irritating comprising expanding the intravascular irritation element in the venous lumen so that the plurality of mechanical irritating objects contact the inner surface.

Optionally, the intravascular irritation element comprising a shape memory element having a regainable geometry, wherein the providing comprises providing the intravascular irritation element in a collapsed state and the irritating comprises allowing the shape memory element to expand toward the regainable geometry in the venous lumen.

Optionally, the irritating comprises rotating the intravascular irritation element approximately around a longitudinal axis of the target lumen.

More optionally, the rotating is performed simultaneously with at least one of pushing and pulling the intravascular irritation element along the longitudinal axis.

Optionally, the irritating comprises maneuvering the intravascular irritation element so that at least one of the mechanical irritating objects is brushed against the inner surface in a helical pattern.

Optionally, the inserting comprises releasing a sclerosing agent in proximity to the inner surface.

Optionally, the inserting comprises withdrawing blood in proximity to the inner surface.

According to some embodiments of the present invention there is provided an intrabody device for collapsing a target vein in a patient. The intrabody device comprises a shaft being insertable into a venous lumen of a target vein and an intravascular irritation element affixed at a distal end of the shaft and having a plurality of mechanical irritating objects. The intravascular irritation element is sized and shaped to be moved in the venous lumen so that the plurality of mechanical irritating objects are in contact with an inner surface of the target vein.

Optionally, the intravascular irritation element is a wire and the plurality of mechanical irritating objects are plurality of bristles protruded therefrom.

Optionally, the wire being made of a memory shape material.

Optionally, the intrabody device further comprises a sheath covering at least the distal end, the intravascular irritation element having a collapsed state for inserting the intravascular irritation element into the sheath and an expanded state for brushing against the inner surface.

Optionally, the intravascular irritation element is a flexible mesh woven from a first wire made of a shape memory material and a second wire having the plurality of mechanical irritating objects affixed thereto.

Optionally, the intrabody device further comprises a controller for simultaneously rotating the intravascular irritation element approximately around a longitudinal axis of the target lumen and at least one of pushing the intravascular irritation element along the longitudinal axis and pulling the intravascular irritation element along the longitudinal axis.

Optionally, the intrabody device further comprises an extraction channel positioned along the shaft and configured for withdrawing blood in proximity to the intravascular irritation element.

More optionally, the extraction channel is configured for performing the withdrawing while the intravascular irritation element is maneuvered.

Optionally, the intrabody device further comprises an ejection channel positioned along the shaft and configured for releasing a medical substance in proximity to the intravascular irritation element.

More optionally, the medical substance comprises a sclerosing agent.

More optionally, the ejection channel is configured for performing the releasing while the intravascular irritation element is maneuvered.

More optionally, the ejection channel is configured for performing the releasing after the intravascular irritation element being maneuvered.

More optionally, the ejection channel is configured for performing the releasing before the intravascular irritation element being maneuvered.

Optionally, the intrabody device further comprises an expandable filter element affixed at a distal end of the intravascular irritation element and configured for filtering blood during the intravascular irritation element being maneuvered in the venous lumen.

According to some embodiments of the present invention there is provided a kit for collapsing a target vein in a patient. The kit comprises a plurality of detachable intravascular irritation element s each configured for moving in contact with an inner surface of a target vein having at least one different anatomical characteristic and a shaft configured for detachably coupling at least one of the plurality of detachable intravascular irritation elements and inserting the coupled detachable intravascular irritation element into a venous lumen.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

The present invention, in some embodiments thereof, relates to method and device for vein treatment and, more particularly, but not exclusively, to a method and a device for vein ablation.

According to some embodiments of the present invention there is provided an intrabody device and a method for collapsing one or more target veins, such as the saphenous vein, in a patient. The method and the device are based on an intravascular irritation element, such as a wire or a mesh of wires, having a plurality of mechanical irritating objects, such as bristles or pins. In use, the intravascular irritation element is inserted into a venous lumen of a target vein and maneuvered by the caretaker, automatically and/or manually, so that an inner surface of the target vein, such as the intima, is irritated by the plurality of mechanical irritating objects which are optionally brushed against it. Such brushing damages the inner surface and therefore triggers a collapse of the target vein, preferably permanently.

Optionally, the device is designed to release one or more medical substances into the venous lumen, in proximity to the inner surface, before, during, and/or after the irritation. In such an embodiment, a sclerosing agent may be released into the venous lumen, in proximity to the inner surface, advancing the collapse of the target vein.

Additionally or alternatively, the device is designed to withdraw blood and/or debris from the venous lumen, in proximity to the inner surface, before, during, and/or after the irritating. In such an embodiment, withdrawing of blood may expedite the collapsing of the target vein and/or prevent from debris and/or the released medical substance from flowing away from the treated area.

Optionally, the device further comprises a filtering element, optionally expandable, for filtering blood in the treated area. In such an embodiment, debris and/or medical substances released during the treatment may be filtered and extracted from the body.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
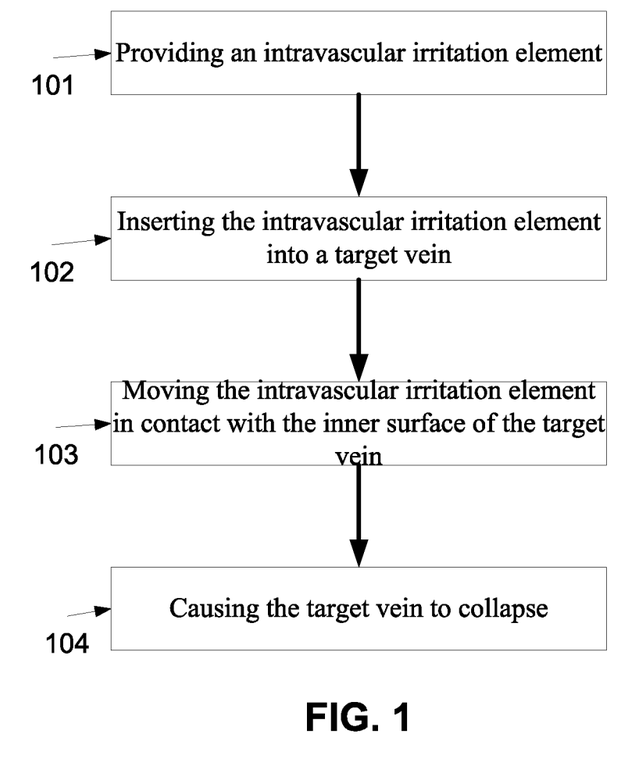
FIG. 1 is a flowchart of a method for collapsing a target vein in a patient for using mechanical irritating objects, according to some embodiments of the present invention.
Figures 6A, 6B:
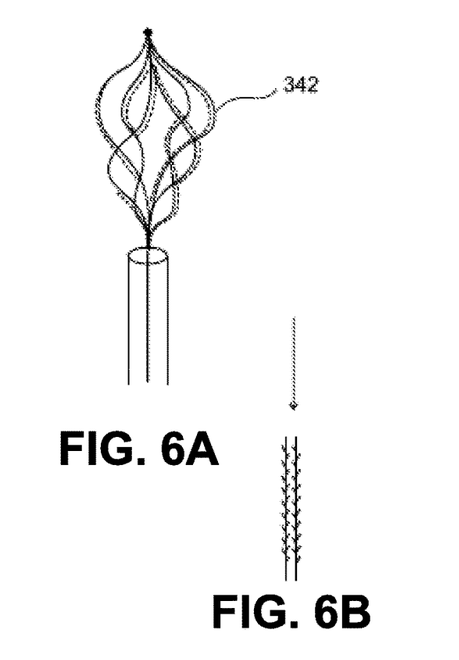
FIG. 6A is a schematic illustration of another intravascular irritation element having an expandable structure, according to some embodiments of the present invention.
FIG. 6B is a schematic illustration of a wire having bristles which may be used for constructing an intravascular irritation element, according to some embodiments of the present invention.

Reference is now made to FIG. 1, which is a schematic illustration of a method for collapsing, preferably permanently, a target vein in a patient using mechanical irritating objects, according to some embodiments of the present invention. As used herein, the target vein may be a perforator vein, a spider vein, a varicose vein, hemorrhoids, varicocele and/or a saphenous vein which is selected by a caretaker for receiving vein ablation treatment. The target vein may be any vein which designated for elimination in any medical and/or cosmetic procedure. As shown at 101, the method is based on an intravascular irritation element having a plurality of mechanical irritating objects. Optionally, the intravascular irritation element is an expandable element having a plurality of mechanical irritating objects, such as bristles, pins, wires, studs, anchors, knives, filers, hooks, and/or any type of scratchers. For example, the mechanical irritating object is a bristle, optionally sharpened, having a length between 0.05 mm and 0.4 mm, for example 0.1 mm. Optionally, the intravascular irritation element is a wire and the mechanical irritating objects bristles, which are affixed thereon, in a variety of directions and combinations in relation to the intravascular irritation element longitudinal axis, for example as depicted in FIG. 6B. Optionally, mechanical irritating objects are inclined in two opposing directions, optionally toward the two opposing tips of the intravascular irritation element. In such an embodiment, the irritation is performed when the mechanical irritating objects are pulled and/or pushed. Optionally, the treatment is performed by maneuvering the intravascular irritation element back and forth along the target vein. The intravascular irritation element is affixed at a distal end of a shaft that is designed to be inserted into a lumen of a target vein. For brevity a device comprising at least a shaft and an intravascular irritation element may be referred to herein as a mechanical vein elimination device.

Figure 2:
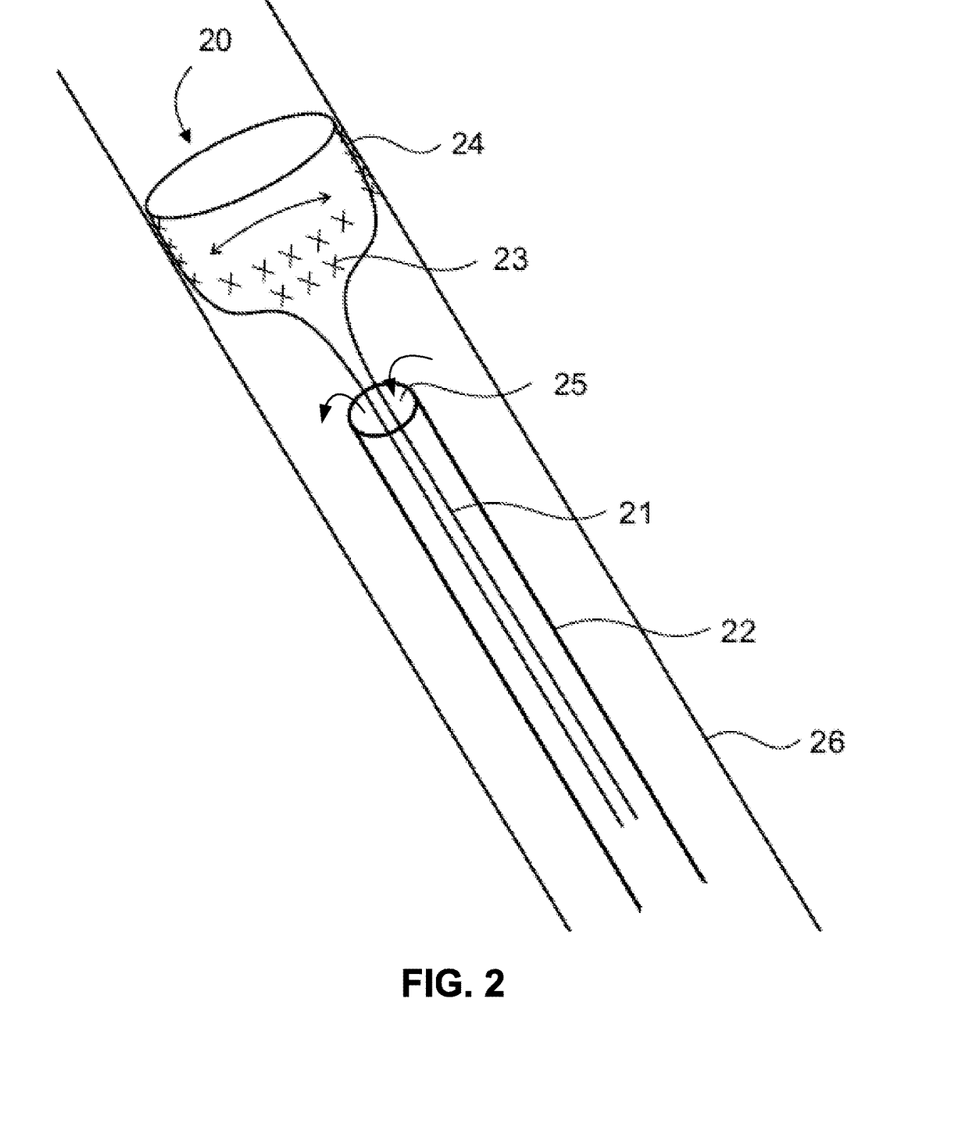
FIG. 2 is a schematic illustration of a distal tip of an exemplary mechanical vein elimination device having a plurality of mechanical irritating objects, according to some embodiments of the present invention.

Reference is now also made to FIG. 2, which is a schematic illustration of a distal tip 20 of an exemplary mechanical vein elimination device 20 having a plurality of mechanical irritating objects 24, according to some embodiments of the present invention. The mechanical vein elimination device 20 comprises a shaft 21 that is optionally encircled by an outer sheath, such as a common catheter sheath. In such an embodiment, the mechanical vein elimination device 20 further comprises a controller, such as a double syringe controller (not shown), for separately controlling the shaft 21 and the sheath 22 along a longitudinal axis which is parallel or substantially parallel to the longitudinal axis of the shaft 21.

The exemplary mechanical vein elimination device 20 further comprises an intravascular irritation element 23 which is affixed, detachably or integrally, to the distal end of the shaft 21. As described above, the intravascular irritation element 23 has a plurality of mechanical irritating objects 24, such as pins, wires, studs and/or any other scratchers arranged to abrade, scratch, peel, or catch, of the inner surface, or intima, of the target vein. The target vein may be in proximity to a venous branch, for example at the inner surface of varicose vein segments in proximity to perforators, such as the mid thigh (hunterian) perforator, the popliteal vein, the Dodd's perforator, and the Boyd's perforator. The intravascular irritation element 23 is optionally sized and shaped, for example as shown in FIG. 2, to allow the plurality of mechanical irritating objects 24 to contact the inner surface of a target vein 26.

Optionally, the intravascular irritation element 23 has a collapsed state, in which it is narrowed for allowing the insertion thereof into the venous lumen and an expanded state for establishing a contact with the inner surface of the target vein 26, as described above. Optionally, the intravascular irritation element 23 is made from a shape memory alloy (SMA), also known as a smart alloy, a memory metal, and/or muscle wire, such as Nickel Titanium (NiTi). In such an embodiment, the intravascular irritation element 23 is designed to switch from the collapsed state to the expanded state by regaining a geometry that is sized to at least contact the inner surface of a target vein, such as the great saphenous vein and/or the small saphenous vein. The ability to regain the geometry allows narrowing the intravascular irritation element 23 while the distal end of the mechanical vein elimination device 20 is positioned in the venous lumen of the target vein. For example, the intravascular irritation element 23 may be held in a narrowed configuration by the inner walls of the sheath 22.

As shown at 102, after the mechanical vein elimination device 20 is provided, as shown at 101, the distal end of the mechanical vein elimination device 20 is inserted with the intravascular irritation element 23, optionally in a collapsed state, into a venous lumen of a target vein. Optionally, the insertion is guided using ultrasound probe, according to a commonly known intravascular ultrasound process.

As shown at 103, when the intravascular irritation element 23 is in target vein, and optionally switched to an expanded state, the mechanical irritating objects are positioned to move in contact with the inner surface of the venous walls. Optionally, the mechanical irritating objects are brushed against the inner surface of the venous walls during this movement. As used herein brushing means brushing, rubbing, scribing, scratching and/or otherwise irritating the inner surface of a vein. Optionally, the movement in contact is performed when the intravascular irritation element 23 is withdrawn from the vein, optionally in a pulling operation. The movement in contact is optionally performed by rotating the intravascular irritation element 23, for example around the longitudinal axis of the shaft 21, which is parallel, optionally in an overlapping manner, to the longitudinal axis of the target vein. Optionally, the intravascular irritation element 23 is simultaneously rotated and pulled or pushed. In such a manner, the movement forms a helical pattern on the inner surface of the target vein. In such an embodiment, the inner surface may be brushed in a helical pattern.

The movement of the mechanical irritating objects in contact with the inner surface scratches, irritates, scribes, peels, catches, and/or otherwise damages the venous walls, for example the intima thereof. As shown at 104, such damage causes the vein to permanently collapse, for example due to the clotting and/or the coagulation of the area. In addition, the damage causes the forming of a scar tissue in the treated area.

Optionally, after the intravascular irritation element 23 is inserted into the target vein, the treatment is provided segment by segment. Each segment may be between 3 and 12 centimeters (cm), for example according to the decision of the caretaker. For example, if the treatment includes ejection of medical substances and/or withdrawing of blood, as further described below, the maneuvering of the intravascular irritation element 23 and the withdrawing and/or the ejection are performed in a number of intervals, optionally consecutive, wherein during each interval a different segment is treated.

It should be noted that in such an embodiment, the vein is eliminated, for example permanently collapsed, without using sclerosing agents, foreign chemicals electromagnetic (EM) radiation, heating and/or freezing techniques and/or laser energy. As no chemicals are used, the likelihood of discoloration or hyper-pigmentation of the skin in proximity to the treated area is reduced and/or eliminated.

It should be noted that as the treatment described herein may not involve using radiating, heating and/or freezing. As such the treatment may be provided as a complementary treatment to area which is sensitive to radiating, heating and/or freezing. In such a manner, some target veins or segments thereof may be treated with radiating, heating and/or freezing while others are treated as described herein.

It should be noted that as the treatment described herein may not include using sclerosing agents. As such, the treatment may be provided to patients which are sestive or allergic to the sclerosing agents.

According to some embodiments of the present invention, there is provided a kit having a shaft 21 and a plurality of detachable intravascular irritation elements. Optionally, each detachable intravascular irritation element is sized and shaped according to the anatomical characteristics of different veins, for example according to the diameter of each vein and/or the presence and/or absence of relatively large venous valves. For example, one detachable intravascular irritation element may be sized and shaped according to the diameter of the great saphenous vein and the other according to the diameter of small saphenous vein. Optionally, each detachable intravascular irritation element 23 is designed for damaging the venous walls, for example the intima thereof, in a different pattern and/or to a different extent. In such a manner, the caretaker may select among low, moderate and/or high levels of damaging the venous walls, from causing minor irritation through an inner peeling or even a vein stripping. For instance, the mechanical irritating objects 24 of each detachable intravascular irritation element 23 may have a different degree of sharpness, a different level of strength, a different degree of flexibility, and/or a different degree angle in relation to the central axis of the intravascular irritation element 23. In such a manner, the caretaker may adjust the pattern to the medical condition of the patient. For example if the patient takes blood thinner, such as Plavix™, a detachable intravascular irritation element 23 that causes less damage is selected, as the clotting pace is relatively slow.

Optionally, the mechanical vein elimination device 20 further comprises an extraction channel for withdrawing blood and/or debris which is released when the venous walls are damaged. The withdrawing is performed before and/or when the mechanical irritating objects irritates the venous walls, for example by being brushed against them. Optionally, the extraction channel is positioned along the shaft 21. Optionally, the extraction channel has a suction opening 25 that is directed toward the intravascular irritation element 23. Optionally, the extraction channel is the lumen between the shaft 21 and the sheath 22 and/or positioned in this lumen. Optionally, the withdrawing of blood from the target vein decreases the volume of blood in the target vein and enabling the released sclerosing agents or drugs, as described below.

Additionally or alternatively, the mechanical vein elimination device 20 further comprises an ejection channel for releasing a medical substance comprising one or more of the following: a sclerosing agent, such as sodium tetradecyl sulfate (STS), polydocanol, and bleomycin, a drug, a medical component, a filling, such as hyaluronic acid (HA) secretion and collagen, a medical agent and/or any combination thereof. The medical substance is released before, during, and/or after the mechanical irritating objects irritate the venous walls. Optionally, the ejection channel is positioned along the shaft 21. Optionally, the ejection channel has a release opening 25 that is directed toward the intravascular irritation element 23. Optionally, the extraction channel is the lumen between the shaft 21 and the sheath 22 and/or positioned in this lumen. Such an ejection channel enables delivery of the medical substance into the lumen in proximity to the damaged venous walls. Optionally, the released medical substance is a sclerosing agent that is designed to shrink the target vein. As the venous walls are damaged by the mechanical irritating object, the sclerosing agent permeability rate is increased. The sclerosing agent penetrates the injured intima, expedite and/or facilitate the occluding thereof. Optionally, the releasing and the withdrawing are synchronized in a manner that allows withdrawing the medical substance after the administration thereof, for example as described in International Patent Application No. PCT/IL209/000197 filed on Feb. 19, 2009, which is incorporated herein by reference.

It should be noted that as venous walls are irritated during the treatment, the amount and/or the concentration of the sclerosing agent may be relatively low in relation to the amount and/or the concentration of the sclerosing agent which are used in a common sclerotherapy procedure. For example, the concentration of the sclerosing agent may be less than the concentration that is used in standard treatments, for example less than 5%, 3% and 1%. Furthermore, in typical sclerotherapy procedures, the vein valve areas pose a greater challenge to ablate as the venous walls are thicker and bulkier than other areas. As such, the amount and/or concentration which are used are typically higher. As the scratching damages the vein valve areas, the amount and/or concentration of sclerosing agents which are used for the ablation of the target vein in these areas may be reduced.

The ejection channel is connected to an ejection force source, such as a piston, for applying an ejection force for conducting the medical substance through the channels. The extraction channel is connected to a suction force source, such as a piston, for applying a suction force for withdrawing blood and/or debris from the venous lumen through the extraction channel.

Optionally, the ejection channel and/or a number of additional ejection channels which are positioned in parallel to the ejection channel may be used for administering additional medical substances in combination to the medical substance which is administered by the ejection channel.

Figure 3:
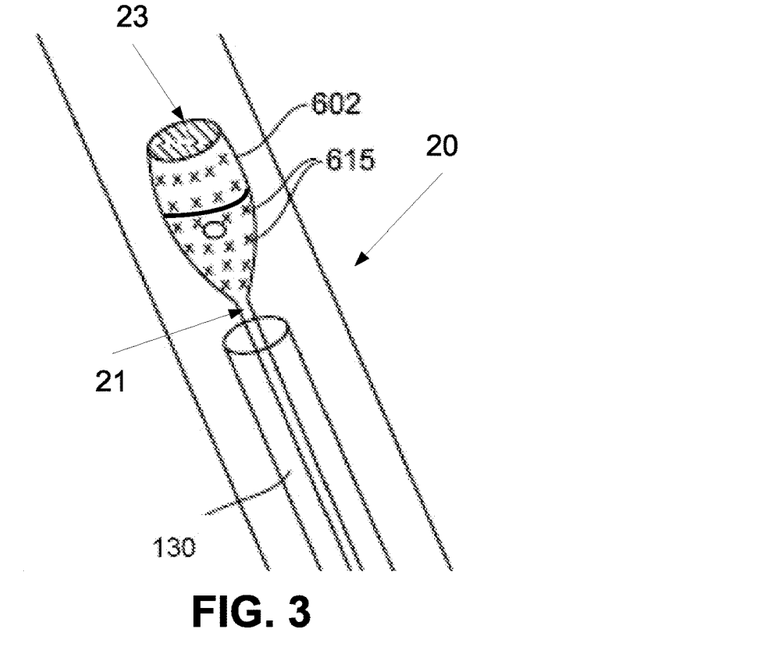
FIG. 3 is a schematic illustration of an intravascular irritation element having a mechanism for releasing a medical substance a before the venous wall is irritated by the intravascular irritation element, according to some embodiments of the present invention.

Reference is now also made to FIG. 3, which is a schematic illustration of an intravascular irritation element 23 having a mechanism for releasing a medical substance 615 before the venous wall is irritated by the intravascular irritation element 23, according to some embodiments of the present invention. The intravascular irritation element 23 is optionally conducted in a catheter deliver that comprises the shaft 21 in a sheath 130.

In such an embodiment, the ejection channel may be integrated into the shaft 21. For example, the shaft 21 may be hollow, having a lumen that functions as an ejection channel. In such a manner, the ejection channel may release the medical substance directly via the intravascular irritation element 23.

In such an embodiment, the intravascular irritation element 23 has one or more releasing areas 615, such as a plurality of outlets, such as apertures and/or nozzles, and a vein scratching area 602 that includes the mechanical irritating objects. As shown in FIG. 3, in use, the vein scratching area 602 is closer to the distal point of mechanical vein elimination device 20, and the releasing area 615 is closer to the proximal side of the mechanical vein elimination device 20, or further upstream in the vein, so that when releasing or extracting device 20 from the target vein, the sclerosing materials may be applied to an area of the vein before the irritating the vein scratching area 602 against the venous walls takes place. In such a manner, when treatment is performed by removing or pulling the mechanical vein elimination device 20 out of the vein, for example against the direction of the blood flow, the medical substance first interact with the venous wall, and subsequently, upon pulling the intravascular irritation element 23 through the treated area, the intravascular irritation element 23 damages the venous wall.

Figure 4:
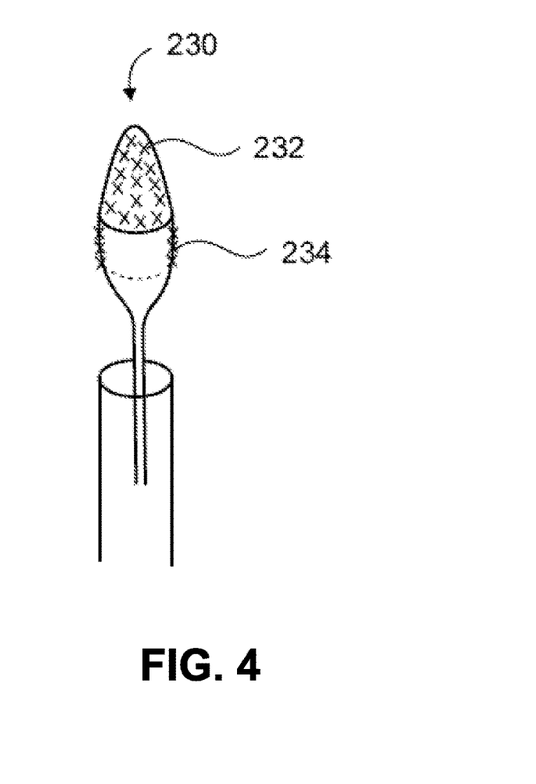
FIG. 4 is a schematic illustration of a mechanical vein elimination device with a mechanism for releasing a medical substance after the venous wall is irritated by the intravascular irritation element, according to some embodiments of the present invention.

Reference is now made to FIG. 4, which is a schematic illustration of a mechanical vein elimination device 230 with a mechanism for releasing a medical substance after the venous wall is brushed with the a vein scratching area 234 of the intravascular irritation element 23, according to some embodiments of the present invention. Similarly to FIG. 3, the mechanical vein elimination device 230 comprises vein scratching area 234 and releasing area 232. However, in FIG. 4, the material releasing area 232 is positioned at the distal end of the intravascular irritation element 23, downstream in relation to the medical material releasing area 232. In such a manner, when treatment is performed by removing or pulling the mechanical vein elimination device 230 from the venous lumen, for example against the direction of the blood flow, the mechanical vein elimination device 230 scratches the venous wall, thereby causing bleeding, coagulation, and scarring the selected area. Then, upon pulling the mechanical vein elimination device 230 through the treated area, the medical substance is released through the holes in material releasing area 232, thereby interact with the damaged venous wall.

Figure 5:
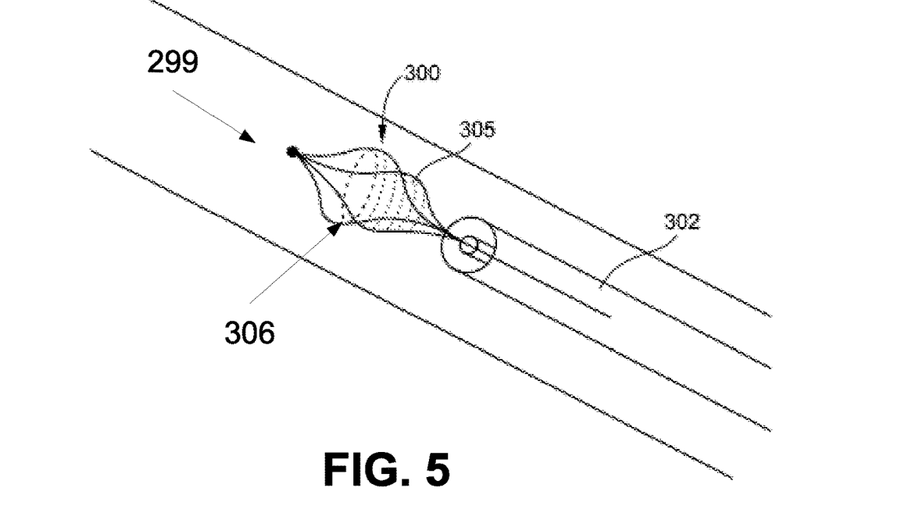
FIG. 5 is a schematic illustration of a tip of a mechanical vein elimination device having an intravascular irritation element that is positioned on an expandable structure, according to some embodiments of the present invention.

Reference is now made to FIG. 5, which is a schematic illustration of a tip of a mechanical vein elimination device 299 having an intravascular irritation element 306 that is positioned on an expandable structure 305, referred to herein cumulatively as an expandable intravascular irritation element 300, according to some embodiments of the present invention. As described above, the intravascular irritation element 300 has a collapsed state, in which it is narrowed for allowing the insertion thereof into the venous lumen and an expanded state for establishing a contact with the inner surface of the target vein 26, as described above. The ability to narrow the expandable intravascular irritation element 300 allows delivering it to a target location using a standard introductory catheter 302 or any other suitable delivery mechanism. The mechanical vein elimination device 300 may include multiple expandable and/or flexible mechanical irritating objects 305 on the intravascular irritation element 306. Optionally, the intravascular irritation element 306 is wire and the mechanical irritating objects 305 are bristles which are connected thereto. The wire is optionally spirally or helically arranged on an expandable structure. The flexible mechanical irritating objects 305 may be constructed from SMA or attached to a structure that is constructed from an SMA or a spring loaded materials. In use, the intravascular irritation element 300 expands toward the venous walls when released from the catheter 302.

In some embodiments mechanical irritating objects 24 may be engraved, etched or cut into one or more flexible arms and/or wires which are set to form an expandable structure, as shown by numeral 342 of FIG. 6A. FIG. 6B is a close up of an exemplary wire. Optionally, coarse elements may be stuck or melted onto the arms, to provide a rough or course surface that can scratch the vein walls/intima.

In other embodiments, the flexible arms and/or wires with the mechanical irritating objects 305 are attached to or positioned above a flexible structure, optionally made from SMA wires. Optionally, the mechanical irritating objects 24 are flexible pins which are perpendicular to the shaft. In such an embodiment, the pins may be bended to diminish the diameter of the intravascular irritation element 23, for example by pulling the shaft 21 into a sheath that encircle it, for example as shown in FIG. 2.

The flexibility and/or expandability of the mechanical irritating objects 24 and/or of a structure that supports them allow scratching a curved inner surface of a target vein. The mechanical irritating objects 24 are diverted toward the venous walls and bended by the curves of the inner surface.

Optionally, the mechanical irritating objects 24 are arranged in a helical or a spiral structure. For example, the mechanical irritating objects 24 may be attached, engraved, etched and/or cut in a wire that is positioned in a helical manner on an expandable structure, as shown in FIG. 5. Such a structure assures that a substantially inner surface of the venous wall is scratched when the intravascular irritation element 23 is pulled and/or pushed along the target vein. Optionally, in use, the intravascular irritation element 23 is designed to regain to a geometry that is wider than the venous lumen of the target vein. In such a manner, when maneuvered, the intravascular irritation element is continually bended against the vein passage surface which limits its expanding. In such manner, narrow and wide vein areas are scratched, for example a narrow vein valve area and a straight inner venous surface may be scratched. Such a treatment allows avoiding unintentional vein perforation or stripping and other undesirable outcomes by limiting the penetration of the device into the intima. The mechanical irritating objects 24 lengths and/or sharpness is designed to avoid excessive damage and/or tear of the target vein.

Optionally, as described above, the intravascular irritation element 23 may be rotated during the pulling and/or the pushing thereof in the venous lumen. In such a manner, a helical scratching pattern is formed and the area of the inner surface of the venous wall that is scratched is increased. In such an embodiment, the likelihood of successfully ablating the target vein is respectively increased.

Figure 7:
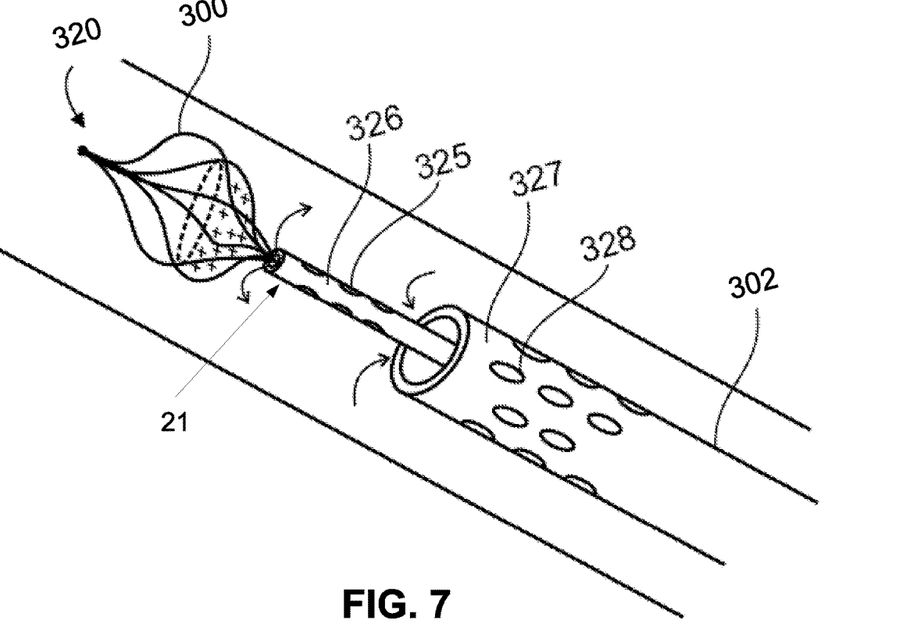
FIG. 7 is a schematic illustration of a tip of a mechanical vein elimination device having an intravascular irritation element that is positioned on an expandable structure and a plurality of inlets and outlets for releasing medical substance and withdrawing blood, according to some embodiments of the present invention.

Reference is now made to FIG. 7, which is a schematic illustration of a mechanical vein elimination device 320, according to some embodiments of the present invention. As depicted in FIGS. 3 and 5, FIG. 7 depicts a mechanical vein elimination device 320 with a sheath 302, a shaft 21, and an intravascular irritation element 300 with an expandable structure 305. Similarly to the described above, the mechanical vein elimination device 320 comprises an ejection channel 326 that is integrated into the shaft 21 and an extraction channel 327 at the lumen between the sheath 302 and the shaft 21. The ejection channel 326 comprises a plurality of outlets 325 which are directed toward the wall of the venous lumen. The extraction channel 327 comprises a plurality of outlets 328 which are directed toward the wall of the venous lumen.

Figure 8:
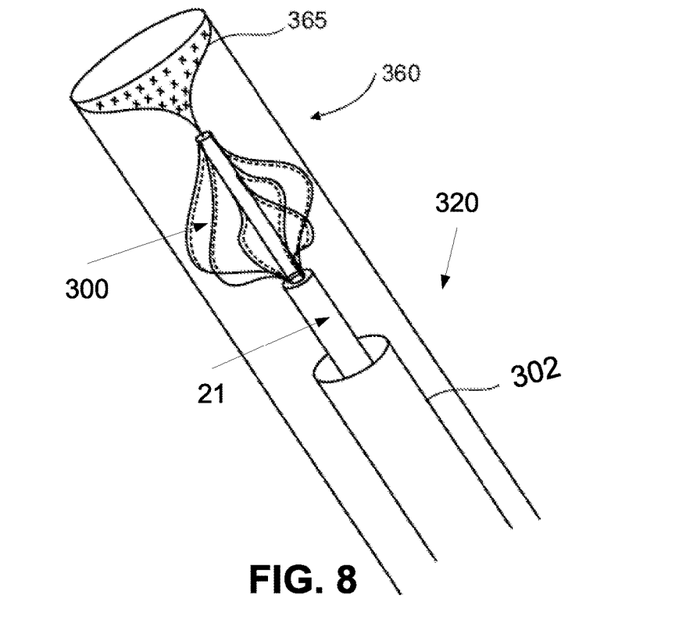
FIG. 8 is a schematic illustration of a mechanical vein elimination device having a filtering element, according to some embodiments of the present invention.

Reference is now made to FIG. 8, which is a schematic illustration of a mechanical vein elimination device 320 having a filtering element 365 for preventing from debris and/or other materials from escaping the area of the treatment and flowing upstream in the vein, according to some embodiments of the present invention. As depicted in FIGS. 3 and 5, FIG. 8 depicts a mechanical vein elimination device 320 with a delivery catheter 363 that includes the sheath 302 and the shaft 21 and with the intravascular irritation element 300. However, in FIG. 8, the mechanical irritating objects 360 are engraved, etched or cut into one or more flexible arms which are positioned in parallel to the central axis of the shaft. In addition, FIG. 8 depicts the filtering element 365. Optionally, the filtering element 365 is designed to capture the debris that is formed by the irritating of the venous walls with the mechanical irritating objects.

The filtering element 365 may be used for blocking, optionally substantially completely, the target vein. For example, the filtering element 365 may be a stent-like mechanism to expand so as to spread across the entire vein circumference, to be substantially impermeable for undesired objects and/or debris. The filtering element 365 may be automatically deployed at the distal end of the mechanical vein elimination device 320, upon releasing the intravascular irritation element 300 from the delivery catheter 363. The filtering element 365 may be substantially impermeable, or may be permeable to certain contents yet impermeable to other contents. For example, the filtering element 365 may allow blood to flow downstream while it filters clots and/or other solid objects having a predefined diameter therefrom. The filtering element 365 may be used for preventing debris and/or clots from flowing downstream before, during and/or after the irritating of the venous walls. Optionally, the mechanical vein elimination device 320 has an ejection channel, for example as described above. In such an embodiment, the filtering element 365 may additionally or alternatively filter medical substances which are released by the ejection channel.

Figures 9A, 9B:
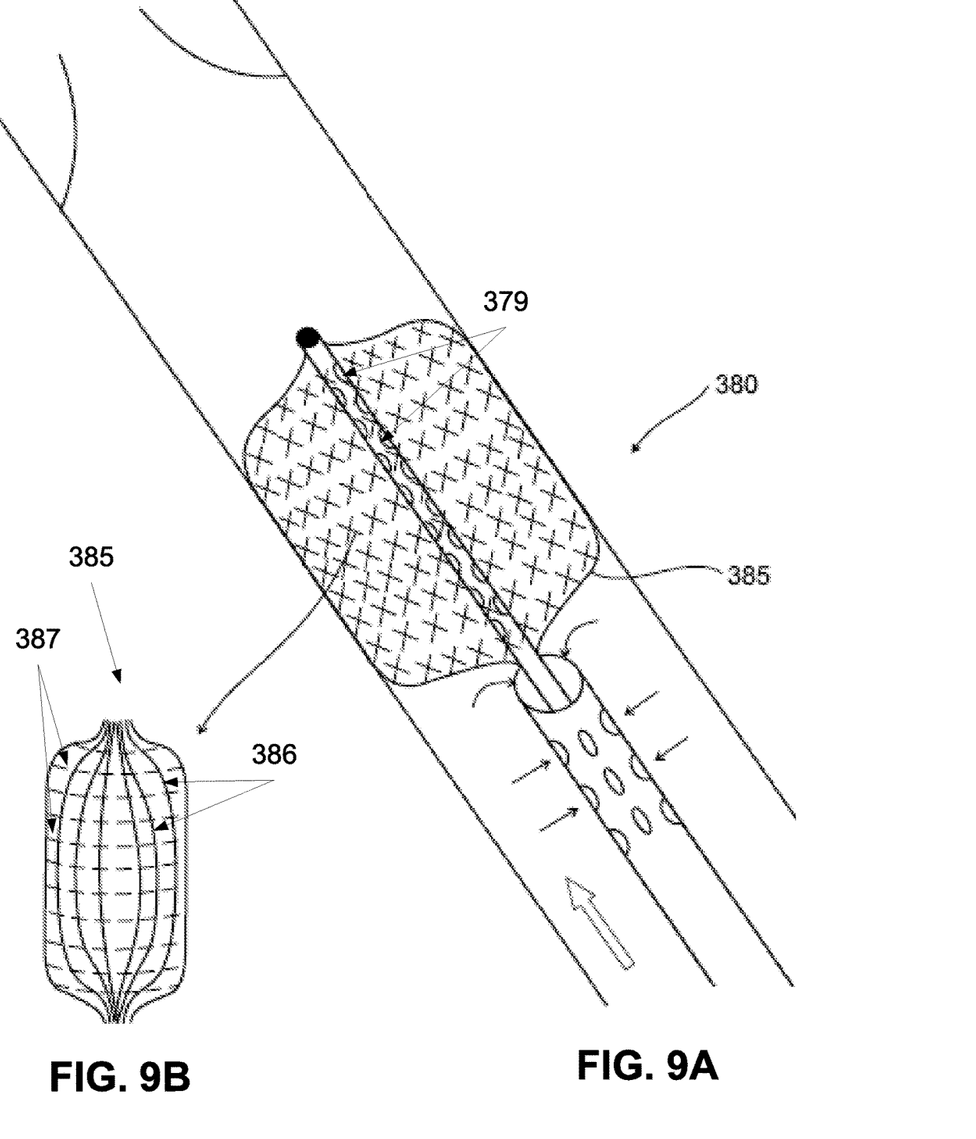
FIG. 9A is a schematic illustration of a mechanical vein elimination device with an intravascular irritation element that includes an expandable mesh, according to some embodiments of the present invention.
FIG. 9B is an intravascular irritation element which is constructed from a woven mesh, according to some embodiments of the present invention.

Reference is now made to FIG. 9A, which is a schematic illustration of a mechanical vein elimination device 380 with an intravascular irritation element that includes an expandable mesh 385, according to some embodiments of the present invention. As depicted in FIGS. 3 and 5, the mechanical vein elimination device 380 of FIG. 9A has a delivery catheter that includes the sheath 302, the shaft 21, and an intravascular irritation element 385. However, as depicted in FIG. 9A, the mechanical vein elimination device 380 includes a plurality of outlets 379 for releasing a medical substance substantially perpendicular to the mechanical irritating objects and the intravascular irritation element 385 thereof comprises a flexible mesh designed to expand so as to contact and scratch the venous walls. Optionally, the mesh 385 is constructed by weaving wires. Optionally, as shown at FIG. 9B, one or more of the wires are memory shape wires, such as an SMA wire 386, for allowing the expanding the intravascular irritation element 385 so as to contact and scratch the venous walls and one or more of the wires includes mechanical irritating objects 387, for example coarse and/or jagged wires. When the mechanical vein elimination device 380 is deployed in a venous lumen, the mesh 385 expands to contact the venous walls. Optionally the mesh 385 is made of one or more memory shape wires which are designed to regain a shape of a cylinder having a diameter that is greater than the diameter of the venous lumen. Thus, in use, the mesh 385 is pushed toward the inner surface of the venous walls, even if the surface features of the venous walls are curved and/or otherwise non linear. Optionally, the mesh has holes for releasing medicinal substances, such as sclerosing agents, from the plurality of outlets 379.

It is expected that during the life of a patent maturing from this application many relevant methods and devices will be developed and the scope of the term a shape memory material, a catheter, and ultrasound guiding is intended to include all such new technologies a priori.

As used herein the term "about" refers to ±10.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method for ablating a target vein in a patient, comprising:
   providing an intravascular irritation element having a woven mesh with a plurality of mechanical irritating objects, said woven mesh is made of one or more memory shape wires and set to expand by regaining a geometry having a diameter that is greater than a diameter of a venous lumen of a target vein, said geometry limits the penetration of said intravascular irritation element into the intima of said venous lumen;
   inserting said intravascular irritation element into said venous lumen using a catheter mechanism having an ejection channel having a plurality of outlets and an extraction channel; and
   irritating said target vein by moving said intravascular irritation element in contact with an inner surface thereof so that a collapse of said target vein being triggered,
   during said irritating performing at least one of releasing a sclerosing agent through said plurality of outlets in proximity to said inner surface and withdrawing blood with said sclerosing agent through said extraction channel in the vein;
   wherein said woven mesh surrounds said plurality of outlets;
   wherein said woven mesh is a flexible mesh having said plurality of mechanical irritating objects affixed thereto and is sized and shaped to expand so as to bring said plurality of mechanical irritating objects to scratch venous walls of said target vein when said intravascular irritation element is moved along said target vein; wherein said woven mesh is sized and shaped to expand so that during said moving said woven mesh continually bended against vein passage surface of said venous lumen which limits its expanding.

2. The method of claim 1, wherein said target vein is the saphenous vein.

3. The method of claim 1, wherein said inserting comprises inserting said intravascular irritation element when being held in by inner walls of a sheath and said irritating comprising expanding said intravascular irritation element in said venous lumen so that said plurality of mechanical irritating objects contact said inner surface.

4. The method of claim 1, wherein said woven mesh is a shape memory element having a regainable geometry, wherein said providing comprises providing said intravascular irritation element in a collapsed state and said irritating comprises allowing said shape memory element to expand toward said regainable geometry in said venous lumen.

5. The method of claim 1, wherein said irritating comprises rotating said intravascular irritation element around a longitudinal axis of said target lumen.

6. The method of claim 5, wherein said rotating is performed simultaneously with at least one of pushing and pulling said intravascular irritation element along said longitudinal axis.

7. The method of claim 1, wherein said irritating comprises maneuvering said intravascular irritation element so that at least one of said mechanical irritating object being brushed against said inner surface in a helical pattern.

8. The method of claim 1, wherein said flexible mesh comprises a member of group consisting of a plurality of memory shape wires, plurality of coarse wires and a plurality of jagged wires.

9. The method of claim 1, wherein said flexible mesh is set to regain a shape of a cylinder having a diameter that is greater than the diameter of the venous lumen of said target vein when unbounded.

10. The method of claim 1, wherein said flexible mesh having a plurality of holes for releasing said sclerosing agent therethrough.

11. An intrabody device for ablating a target vein in a patient, comprising:
   a shaft being insertable into a venous lumen of a target vein;
   an intravascular irritation element affixed at a distal end of said shaft and having a woven mesh with a plurality of mechanical irritating objects, said woven mesh is made of one or more memory shape wires to expand by regaining a geometry having a diameter that is greater than a diameter of said venous lumen;
   an ejection channel positioned along said shaft to release a medical substance via a plurality of outlets in proximity to said intravascular irritation element; and
   an extraction channel positioned along said shaft to withdraw blood with said medical substance in the vein;
   wherein said intravascular irritation element is sized and shaped to be moved in said venous lumen so that said plurality of mechanical irritating objects are in contact with an inner surface of said target vein;
   wherein said woven mesh surrounds said plurality of outlets;
   wherein said woven mesh is a flexible mesh having said plurality of mechanical irritating objects affixed thereto and is sized and shaped to expand so as to bring said plurality of mechanical irritating objects to scratch venous walls of said target vein when said intravascular irritation element is moved along said target vein by regaining a geometry having a diameter greater than a diameter of said venous lumen such that when said woven mesh is maneuvered in said venous lumen, said woven mesh continually bended against vein passage surface of said venous lumen which limits its expanding;

wherein said geometry limits a penetration of said intravascular irritation element into the intima of said lumen when said woven mesh continually bended against vein passage surface of said venous lumen.

12. The intrabody device of claim 11, wherein said woven mesh is weaved from a wire and said plurality of mechanical irritating objects are plurality of bristles protruded therefrom.

13. The intrabody device of claim 12, wherein said wire is made of a memory shape material.

14. The intrabody device of claim 13, wherein said extraction channel is formed in the lumen between said shaft and a sheath covering said shaft.

15. The intrabody device of claim 11, further comprising a sheath covering at least said distal end, said intravascular irritation element having a collapsed state for inserting said intravascular irritation element into said sheath and an expanded state for brushing against said inner surface.

16. The intrabody device of claim 11, wherein said woven mesh is a flexible mesh woven from a first wire made of a shape memory material and a second wire having said plurality of mechanical irritating objects affixed thereto.

17. The intrabody device of claim 11, further comprising a controller for simultaneously rotating said intravascular irritation element around a longitudinal axis of said target lumen and at least one of pushing said intravascular irritation element along said longitudinal axis and pulling said intravascular irritation element along said longitudinal axis.

18. The intrabody device of claim 11, wherein said extraction channel is configured for performing said withdrawing while said intravascular irritation element being maneuvered.

19. The intrabody device of claim 11, wherein said medical substance comprises a sclerosing agent.

20. The intrabody device of claim 11, wherein said ejection channel is configured for performing said releasing while said intravascular irritation element being maneuvered.

21. The intrabody device of claim 11, wherein said ejection channel is configured for performing said releasing after said intravascular irritation element being maneuvered.

22. The intrabody device of claim 11, wherein said ejection channel is configured for performing said releasing before said intravascular irritation element being maneuvered.

23. The intrabody device of claim 11, further comprising an expandable filter element affixed at a distal end of said intravascular irritation element and configured for filtering blood during said intravascular irritation element being maneuvered in said venous lumen.

24. The intrabody device of claim 11, wherein said ejection channel having at least one release opening directed toward said intravascular irritation element.

25. The intrabody device of claim 11, wherein said ejection channel is integrated into said shaft.

26. The intrabody device of claim 11, wherein said plurality of outlets are directed toward the wall of said target vein.

27. An intrabody device for ablating a target vein in a patient, comprising:
a shaft being insertable into a venous lumen of a target vein;
an ejection channel positioned along said shaft to release a medical substance via a plurality of outlets; and
a flexible woven mesh made of one or more memory shape wires and set to expand by regaining a geometry having a diameter that is greater than a diameter of said venous lumen; wherein said geometry limits a penetration of said flexible woven mesh into the intima of said lumen when said woven mesh continually bended against vein passage surface of said venous lumen;
mounted at a distal end of said shaft so as to surround said plurality of outlets and having a plurality of mechanical irritating objects affixed thereto;
wherein said flexible mesh is sized and shaped to expand such that when said woven mesh is moved by said shaft along said target vein, said woven mesh continually bended against vein passage surface of said venous lumen which limits its expanding and scratches the venous walls of said target vein with said mechanical irritating objects;
wherein said woven mesh is a flexible mesh having said plurality of mechanical irritating objects affixed thereto and is sized and shaped to expand so as to bring said plurality of mechanical irritating objects to scratch venous walls of said target vein when said flexible woven mesh is moved along said target vein.

* * * * *